US006554859B1

(12) United States Patent
Lang et al.

(10) Patent No.: US 6,554,859 B1
(45) Date of Patent: Apr. 29, 2003

(54) ACCOMMODATING, REDUCED ADD POWER MULTIFOCAL INTRAOCULAR LENSES

(75) Inventors: Alan J. Lang, Long Beach, CA (US); Arlene Gwon, Newport Beach, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/565,036

(22) Filed: May 3, 2000

(51) Int. Cl.[7] .................................................. A61F 2/16
(52) U.S. Cl. ..................... 623/6.28; 623/6.32; 623/6.34
(58) Field of Search ............................... 623/6.24, 6.27, 623/6.28, 6.37–6.4, 6.44, 6.32–6.34

(56) References Cited

U.S. PATENT DOCUMENTS

| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |

(List continued on next page.)

FOREIGN PATENT DOCUMENTS

| AU | 3225789 | 10/1989 |
| CH | 8902251 | 3/1989 |
| DE | 2702117 | 7/1978 |
| DE | 3246306 | 6/1984 |
| EP | 939016 | 10/1963 |
| EP | 0246216 | 11/1987 |
| EP | 0329981 | 8/1989 |
| EP | 337390 | 10/1989 |

(List continued on next page.)

OTHER PUBLICATIONS

Thornton, Color Atlas of Lens Implantation, Accommodation in Pseudophakia, pp. 159–162, 1991.

Menezo, et al. J Cataract Refract Surg 24, Aug. 1998.

Fechner, et al. J Cataract Refract Surg 24, Jan. 1998.

(List continued on next page.)

Primary Examiner—David J. Isabella
Assistant Examiner—Urmi Chattopadhyay
(74) Attorney, Agent, or Firm—Stout, Uxa, Buyan & Mullins, LLP; Frank J. Uxa; Peter Jon Gluck (57) ABSTRACT

An intraocular lens for implantation in an eye of a patient includes a multifocal optic and a movement assembly. The optic has maximum add power which is less than the add power required for full near vision for a pseudophakic eye. The movement assembly is coupled to the optic and is adapted to cooperate with the eye of the patient to effect accommodating movement of the optic in the eye. Lens systems including two optics and two movement assemblies are also provided. The intraocular lenses and lens systems are particularly useful when implanted in the eyes of a patient after removal of the natural lenses.

19 Claims, 6 Drawing Sheets

U.S. PATENT DOCUMENTS

| | | |
|---|---|---|
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Neilsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,702,244 A | 10/1987 | Mazzocco |
| 4,704,016 A | 11/1987 | De Carle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Hom et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Miege et al. |
| 4,976,732 A | 12/1990 | Vorosmarth |
| 4,990,159 A | 2/1991 | Kraff |
| 4,994,082 A | 2/1991 | Richards et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,074,877 A | 12/1991 | Nordan |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,236,452 A | 8/1993 | Nordan |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,702,440 A | 12/1997 | Portney |
| 5,766,244 A | 6/1998 | Binder |
| 5,769,890 A | 6/1998 | McDonald |
| 5,776,191 A | 7/1998 | Mazzocco |
| 5,800,533 A | 9/1998 | Eggleston et al. |
| 5,814,103 A | 9/1998 | Lipshitz et al. |
| 5,843,188 A | 12/1998 | McDonald |
| 5,847,802 A | 12/1998 | Menezes et al. |
| 5,864,378 A | 1/1999 | Portney |
| 5,876,442 A | 3/1999 | Lipshitz et al. |
| 5,898,473 A | 4/1999 | Seidner |
| 5,929,969 A | 7/1999 | Roffman |
| 6,013,101 A | 1/2000 | Israel |
| 6,096,078 A | 8/2000 | McDonald |
| 6,110,202 A | 8/2000 | Barraquer et al. |
| 6,176,878 B1 | 1/2001 | Gwon et al. |
| 6,197,058 B1 | 3/2001 | Portney |
| 6,217,612 B1 | 4/2001 | Woods |
| 6,231,603 B1 * | 5/2001 | Lang et al. ................ 623/6.37 |

FOREIGN PATENT DOCUMENTS

| | | |
|---|---|---|
| EP | 0342895 | 11/1989 |
| EP | 0351471 | 1/1990 |
| EP | 0480748 | 4/1992 |
| EP | 0566170 | 10/1993 |
| EP | 0691109 | 1/1996 |
| EP | 0780718 | 6/1997 |
| EP | 0897702 | 2/1999 |
| FR | 0488835 | 6/1992 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| IL | 2058391 | 4/1981 |
| WO | 8603981 | 7/1986 |
| WO | 8700299 | 1/1987 |
| WO | 8707496 | 12/1987 |
| WO | 8911672 | 11/1989 |
| WO | 91/09336 | 6/1991 |
| WO | 0488835 | 6/1992 |
| WO | 9416648 | 8/1994 |
| WO | 9503783 | 2/1995 |
| WO | 96/10968 | 4/1996 |
| WO | 9615734 | 5/1996 |
| WO | 9625126 | 8/1996 |
| WO | 97/12272 | 4/1997 |
| WO | 9743984 | 11/1997 |
| WO | 98/21621 | 5/1998 |
| WO | 98/49594 | 11/1998 |
| WO | 98/049594 | 11/1998 |
| WO | 98/56315 | 12/1998 |
| WO | 99/03427 | 1/1999 |
| WO | 99/29266 | 6/1999 |
| WO | 99/028266 | 6/1999 |
| WO | 00/46629 | 8/2000 |
| WO | 00/66039 | 11/2000 |
| WO | 0134067 | 5/2001 |

OTHER PUBLICATIONS

World Optics Inc. Ophthalmology Times, Mar. 15, 1995.

Lolab Corp, Ophthalmology Times, Mar. 15, 1995.

Universe IOL Center, Ocular Surgery News Int'l, No Date Given.

Hanita Lenses, Ocular Surgery News Int'l, No Date Given.

Alcon Surgical, Alcon Laboratories, No Date Given.

Mediphacos LTDA. Ocular Surgery News, Int'l, No Date Given.

Storz Ophthalmics, Inc., Model L122UV Acl. No Date Given.

Opthalmed Inc. OMAC–260, No Date Given.

Chauvin–OPSIA, Axurite ACL (0459) No Date Given.

AMO Specs, Model AC–21B, 1992.

Chiron, Clemente Optifit Modell SPSP525 Brochure Translation, 12/1998.

Chrion Vision, Nuvita MA20, 1997.

Video Tape "New Elliptical Acco. Iol For Cataract Surgery" Shown at ASCRS Symposium on Apr. 10, 1999 (Video Enclosed).

Partial Program Re: ASCRS Symposium, Showing Video Tape Shown Between Apr. 10–14, 1999.

Jacobi, MD., et al, Arch Opthalmol, vol. 117, pp. 17–23, Jan., 1999.

IOL Technologie Brochure, MF3 The Autofocus Lens, 1995.

Jacobi, MD., et al, Arch Ophthalmol, vol. 117, pp. 17–23, Jan., 1999.

IOL Technologie Brochure, MF4 The Autofocus Lens, 1995.

* cited by examiner

ACCOMMODATING, REDUCED ADD POWER MULTIFOCAL INTRAOCULAR LENSES

BACKGROUND OF THE INVENTION

The present invention is directed to intraocular lenses (IOLs). More particularly, the invention relates to multifocal IOLs which are adapted to provide accommodating movement in the eye and which have reduced add powers.

The human eye includes an anterior chamber between the cornea and iris, a posterior chamber, defined by a capsular bag, containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near and distant vision, respectively. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently, multifocal IOLs have been used to provide near/far vision correction. See, for example, Portney U.S. Pat. No. 5,225,858, Roffman et al U.S. Pat. No. 5,448,312 and Menezes et al U.S. Pat. No. 5,682,223. Monofocal IOLs with a depth of focus features has been suggested and are shown and described in Portney U.S. Pat. No. 5,864,378.

Another approach to overcoming loss of accommodation is to use ophthalmic lenses, such as contact lenses or IOLs, with different optical characteristics for each eye. For example with a system known as monovision one lens has a distance vision correction power and the other lens has a near vision correction power. Another example is shown and described in Roffman et al U.S. Pat. No. 5,485,228. It is also known to implant a distant dominant multifocal IOL in one eye and a near dominant multifocal IOL in the other eye as disclosed in the January 1999 issue of Clinical Sciences by Jacobi et al entitled"Bilateral Implantation of Asymmetrical Diffractive Multifocal Intraocular Lenses," pages 17–23.

Whether monovision or multifocal ophthalmic lenses are employed, nighttime images may not be the same for both eyes and/or possess halos as when the headlights of an oncoming vehicle are observed. This can significantly reduce the ability of the observer to identify and locate objects near the headlights. For example, halos tend to be created when the patient views a distant object through the near vision portion of the lens, and the greater the add power, the more perceptible is the halo.

For example, this is shown and described in commonly assigned application Ser. No. 09/302,977 filed on Apr. 30, 1999. This application discloses a reduced add power multifocal IOL which reduces the effects of halos. This reduced add power IOL is implanted in a phakic eye in which the natural lens has lost some degree of accommodation, i.e. in partially presbyopic eyes.

Commonly assigned application Ser. No. (Atty. Docket No.: D-2857) filed concurrently herewith also discloses multifocal reduced add power lenses, such as IOLs, which are asymmetric, i.e., have different optical characteristics. However, one of these lenses has an add power for full near vision.

The disclosure of each of the patent applications and patent identified herein is incorporated in its entirety herein by reference.

SUMMARY OF THE INVENTION

New multifocal intraocular lenses (IOLs) adapted to provide accommodating movement in the eye and which have reduced add powers have been discovered. Such IOLs are particularly useful in aphakic eyes in which the natural lens has been removed. The present IOLs have multiple optical powers, that is are multifocal, have at least one reduced add power and provide substantial benefits. The combination of a multifocal IOL with at least one reduced add power together with the ability of the IOL to move to provide accommodation very effectively provides for enhanced vision over a relatively wide range of distances, for example, from distance through near, and, in addition, reduces the size and/or occurrence of halos and other nighttime vision phenomena which can adversely affect vision.

In one broad aspect of the present invention, intraocular lenses for implantation in an eye of a patient are provided. Such lenses comprise a multifocal optic having a maximum add power which is less than the add power required for full near vision for the pseudophakic eye, that is an eye including the IOL but not including the natural lens. The maximum add power of the multifocal optic preferably is about the add power required for intermediate vision for a pseudophakic eye. In addition, a movement assembly is provided. This movement assembly is coupled to the optic and is adapted to cooperate with the eye of the patient to effect accommodating movement of the optic in the eye.

In one embodiment, the multifocal optic has add powers for providing distance and intermediate vision for a pseudophakic eye and the movement assembly provides sufficient accommodating movement of the optic to obtain near vision for a pseudophakic eye. Thus, the patient in whose eye the present IOL is implanted has a range of vision from distance through near.

As can be seen, the present IOLs utilize a combination of an optic with multifocal characteristics and a movement assembly adapted to provide accommodating movement of the optic in the eye. This combination very effectively provides vision over a range of distances. At the same time, the present IOLs reduce the size and/or occurrence of halos and other nighttime phenomena which can adversely affect the vision of the patient. Such reductions in the size and/or occurrence of one or more of such phenomena are relative to a full add power, for example, full near add power, multifocal IOL located in a fixed position, that is without accommodating movement, in the eye.

To illustrate the present invention, the maximum add power of the present multifocal optic is, for example, no more than about 1.25 diopters or about 1.5 diopters, and the movement assembly is adapted to provide at least about 1.0 diopter or at least about 1.5 diopters of accommodation. Thus, the total or maximum effective optical add power apparent to the patient is about 2.25 diopters or about 3.0 diopters or more, which is well within the range of full near vision. All of the add powers set forth herein are in the spectacle plane.

The movement assembly preferably is adapted to provide at least about 0.5 mm or at least about 0.75 mm of accommodating movement.

In one embodiment, the optic has a distance vision correction power for infinity, for example, with the optic in the rest position or in the unaccommodated state in the eye.

The movement assembly of the present IOLs can be of any configuration suitable to provide the desired accommodating movement. One particularly useful movement assembly is that shown and described in commonly assigned application Ser. No. 09/532,910, filed Mar. 22, 2000.

In one useful embodiment, the movement assembly circumscribes the optic and comprises a member including a proximal end region coupled to the optic and a distal end region extending away from the optic and adapted to contact a capsular bag of the eye. The movement assembly preferably is positioned relative to the optic so that, with the intraocular lens at rest, the optic vaults anteriorly of the distal end region of the movement assembly. In order to enhance the accommodating movement of the present IOLs, the movement assembly may include a hinge assembly positioned proximally of the distal end region.

The present intraocular lenses are preferably deformable for insertion through a small incision in the eye.

In a further broad aspect of the present invention, intraocular lenses are provided which include a multifocal optic having a range of optical powers which can provide vision for a pseudophakic eye of only a portion of the range of from distance through near. A movement assembly, coupled to the optic is provided. This movement assembly is adapted to cooperate with the eye of the patient to effect accommodating movement of the optic in the eye. The accommodating movement is sufficient to provide vision for a pseudophakic eye for the remainder of the range of distance through near whereby the patient has a range of vision from distance through near. Preferably, one of the powers of the optic is a power for distance vision, for example, a distance vision correction power for infinity, for a pseudophakic eye and another of the powers of the optic is an add power.

In a still further broad aspect of the present invention, intraocular lenses for implantation in an eye of a patient are provided and comprise an optic and a movement assembly. The movement assembly is coupled to the optic and adapted to cooperate with the eye of the patient to effect accommodating movement of the optic in the eye. The optic has a baseline optical power and at least one optical add power. The at least one optical add power has a magnitude which is reduced to take into account the accommodating movement provided by the movement assembly. Preferably, the at least one add power has a magnitude which is reduced relative to an add power of a similar optic adapted to be maintained in a fixed position in an eye.

One additional broad aspect of the present invention provides for ophthalmic lens systems for implantation in the eyes of patients, for example, in the eyes of patients whose natural lenses have been removed. Such lens systems comprise first and second multifocal optics. Each of these multifocal optics have an add power. The maximum add power of the first optic is less than the add power required for full near vision for a pseudophakic eye. First and second movement assemblies are provided and are coupled to the first and second optics, respectively. These movement assemblies are adapted to cooperate with the eyes, respectively, of the patient to effect accommodating movement of the first and second optics. The optical characteristics of the first and second optics can be identical or substantially identical or can be different.

In one embodiment, each of these optics have an optical axis. The power of each of these optics changes along a power curve, preferably in a radially outward direction from the associated optical axis. The power curve for the first optic may be different from the power curve for the second optic. Alternately, the power curve for the first optic is substantially the same as the power curve for the second optic.

In one useful embodiment, the first optic is biased for distance vision and the second optic is biased for intermediate vision.

Thus, the first optic or lens is biased for distance vision or is distance biased. This may be accomplished, for example, by configuring the first optic so that the best visual acuity provided by the optic is for distant objects, for example, objects at infinity. The first optic provides better visual acuity for objects at infinity than the second optic. Preferably, the first lens substantially optimizes visual acuity from distance to intermediate distances. The first optic has a power including a power required for distance vision correction for the pseudophakic patient.

The second optic has a power including a power required for intermediate vision correction for the patient. The second optic preferably is intermediate biased. This may be accomplished, for example, by configuring the second optic so that the best visual acuity provided by the second optic is for objects at intermediate distances. Alternatively, or in addition thereto, the second optic provides better visual acuity from intermediate to near distances than the first optic. Preferably, the second optic enhances visual acuity from intermediate to near distances. In addition to the advantages noted above, this enhanced visual acuity of the second optic significantly enhances intermediate vision and provides functional near image quality. It also minimizes potential undesirable effects by using only a low level of image quality disparity between the images received by the two eyes.

The optics or lenses can be made to have the relatively larger ranges in various ways. For example, this can be accomplished by appropriately splitting the light between distance and intermediate. Thus, the second optic may focus sufficient light to an intermediate focus region so as to contribute to the second optic providing enhanced vision from intermediate to near distances.

Alternatively or in addition thereto, the depth of focus of the zone or zones of the optic which provide intermediate vision correction may be appropriately increased to make the second optic have enhanced vision from intermediate to near distances. This may be accomplished, for example, by controlling the aspheric surface design of the optics. More specifically, the second optic may have a zone with an add power for intermediate vision correction with such zone having optical aberrations which increase the depth of focus of such zone. In one preferred embodiment, such zone extends radially outwardly and has progressively increasing add powers as the zone extends radially outwardly.

The add power of the optics is reduced over what it would be if one or both of the optics had the full or even nearly full add power required for near vision correction. The reduced add power significantly reduces halos and/or other nighttime phenomena.

In the interest of keeping the add power low while providing adequate vision quality, preferably the maximum power of any region of either or both of the first and second optics is no greater than about the power required for intermediate vision correction. By way of example, the maximum add power for both the first lens and second lenses may be from about 0.5 diopter to about 1.75 diopters and is preferably from about 1 diopter to about 1.5 diopters.

The first and second optics are adapted to provide some depth of focus. The first optic preferably provides some depth of focus toward intermediate vision correction and preferably the second lens also provides some depth of focus from intermediate vision correction toward far vision correction.

Each of the first and second optics has an optical axis. Preferably the power of the first lens is different at a plurality of locations radially outwardly of the optical axis of the first optic, and the power of the second optic is different at a plurality of locations radially outwardly of the optical axis of the second optic.

Viewed from a different perspective, the power of each of the first and second optics changes along a power curve, for example, in a radially outward direction from the associated optical axis. The power curve for the first optic is different from the power curve for the second optic. The power curve of the first optic may at least contribute to the first lens having good visual acuity from distance to intermediate distances and the power curve of the second optic may at least contribute to the second lens having good visual acuity from intermediate to near distances. Each of the first and second optics may have a power which varies from about the power required for far vision correction to about a power required for intermediate vision correction. In one embodiment, the first optic has a larger range of vision for distance to intermediate distances than the second optic. In the same or a different embodiment, the second optic has a larger range of vision for intermediate to near distances than the first optic.

In one preferred embodiment, the first optic has first, second and third optical zones arranged radially with respect to the optical axis of the first optic with the second zone being intermediate or between the first and third zones and having a greater add power than either of the first and third zones. Similarly, the second optic has first, second and third optical zones arranged radially with respect to the optical axis of the second lens with the second zone being intermediate the first and third zones and having a greater add power than either of the first and third zones of the second optic.

Although the zones can be of various configurations, they are preferably substantially annular and substantially concentric. Preferably, there are at least two zones. Still more preferably, there are three or five of the zones with the innermost and outermost of the zones having a power for far vision correction.

The power in a radial direction can change either gradually or abruptly. The maximum power in each of the second zones may be substantially the same. In one form of the invention, each of the second zones has a power which is substantially constant, and the area, for example, the annular area, of the second zone of the second optic is larger than the area of the second zone of the first optic. This also contributes to the second optic having better visual acuity from intermediate to near than the first lens.

IOLS constructed in accordance with this invention are particularly effective when implanted following removal of the natural lenses. Even though the lenses of this invention have a reduced add power, the additional accommodation provided by the movement assemblies cooperating with the eyes allows excellent visual quality from distance through near.

According to one aspect of the method of this invention first and second IOLs, for example, having different optical characteristics, are implanted in the eyes, respectively, of the patient, preferably after the natural lenses of the patient have been removed. Each of the IOLs preferably has a power required for far vision correction and a power required for intermediate vision correction power with the maximum power of each of the first and second IOLs being less than the add power required for near vision correction for the patient.

According to another feature of the method of this invention, first and second ophthalmic lenses are placed in the eyes of a patient after removal of the natural lenses with the first lens being distance biased and the second lens being intermediate biased.

Each and every feature described herein, and each and every combination of two or more of such features, is included within the scope of the present invention provided that the features included in such a combination are not mutually inconsistent.

The invention, together with additional features and advantages thereof, may best be understood by reference to the following description taken in connection with the accompanying illustrative drawings.

DESCRIPTION OF THE PREFERRED EMBODIMENT

Referring now to FIGS. 1 to 6A, an IOL according to the present invention, shown generally at 10, includes a lens body or optic 12. Extending radially outwardly from lens body 12 is member 14, which fully or completely circumscribes the lens body. Member 14, which includes no through holes, has a proximal end portion 16 which is coupled to the optic 12 at optic periphery 18. Member 14 extends radially outwardly to a distal end region 20 including a peripheral edge 22, which extends between the anterior surface 24 and the posterior surface 26 of member 14. Although it is not essential, member 14 can be, and preferably is, integral or unitary with the optic 12. Member 14 extends outwardly from optic 12 sufficiently so that the distal end region 20 is in contact with the inner peripheral wall of the posterior capsular bag when the IOL 10 is implanted in the eye.

Member 14 is adapted to cooperate with the eye of the patient to provide effective accommodating movement. Member 14 is one example of a useful movement assembly in accordance with the present invention. The movement assembly may be of any suitable construction and configuration provided that it cooperates with the eye to effect the desired accommodating movement. For example, in one embodiment, the movement assembly comprises at least one biasing member, and preferably a plurality of biasing members, coupled to the lens body. The biasing member can be a spring or similar element. The movement assembly can be as disclosed in Levy U.S. Pat. No. 4,409,691, noted previously. The movement assembly may comprise at least one fixation member, and preferably a plurality of fixation members, including a proximal end region coupled to the lens body and a distal end region extending away from the lens body and adapted to contact a capsular bag, for example, the posterior capsular bag, of the mammalian eye. In this embodiment, the action of the eye, for example, the ciliary muscle and/or the zonules, preferably acts directly on the fixation member or members which transfer the force to the lens body causing the accommodating movement of the lens body. A representative movement assembly including fixation members is set forth in the above-noted Cumming U.S. Pat. Nos. 5,674,282 and 5,496,366.

One or more different approaches can be employed to couple the distal end region of the movement assembly to the capsular bag. Examples of such approaches include the use of adhesives, fibrosis of the capsular bag, suturing and the like surgical techniques, and combinations thereof. The movement assembly need not be secured to the capsular bag.

Movement assemblies, such as member 14 are described in more detail in commonly assigned application Ser. No. 09/532,910 filed Mar. 22, 2000.

The member 14, as shown, is integral (unitary) with and circumscribes the optic 12. Alternately, member 14 can be mechanically or otherwise physically coupled to optic 12. The member 14 may only partially circumscribe the optic, and such embodiment is included within the scope of the present invention. The member 14 may be constructed of the same or different biocompatible materials as optic 12, and preferably is made of polymeric materials, such as polypropylene, silicone polymeric materials acrylic polymeric materials and the like. Member 14 has sufficient strength or rigidity to be effective to transfer the force from the capsular bag of the eye to move the optic 12 axially in the eye to effect accommodation. Such strength or rigidity is enhanced by employing a solid member 14, that is a member having no axial through hole or holes, for example, perforations. The member 14 preferably is deformable, in much the same manner as optic 12 is deformable, to facilitate passing IOL 10 through a small incision into the eye. The material or materials of construction from which member 14 is made are chosen to provide the member with the desired mechanical properties, e.g., strength, and/or deformability, to meet the needs of the particular application involved.

Figure 6:
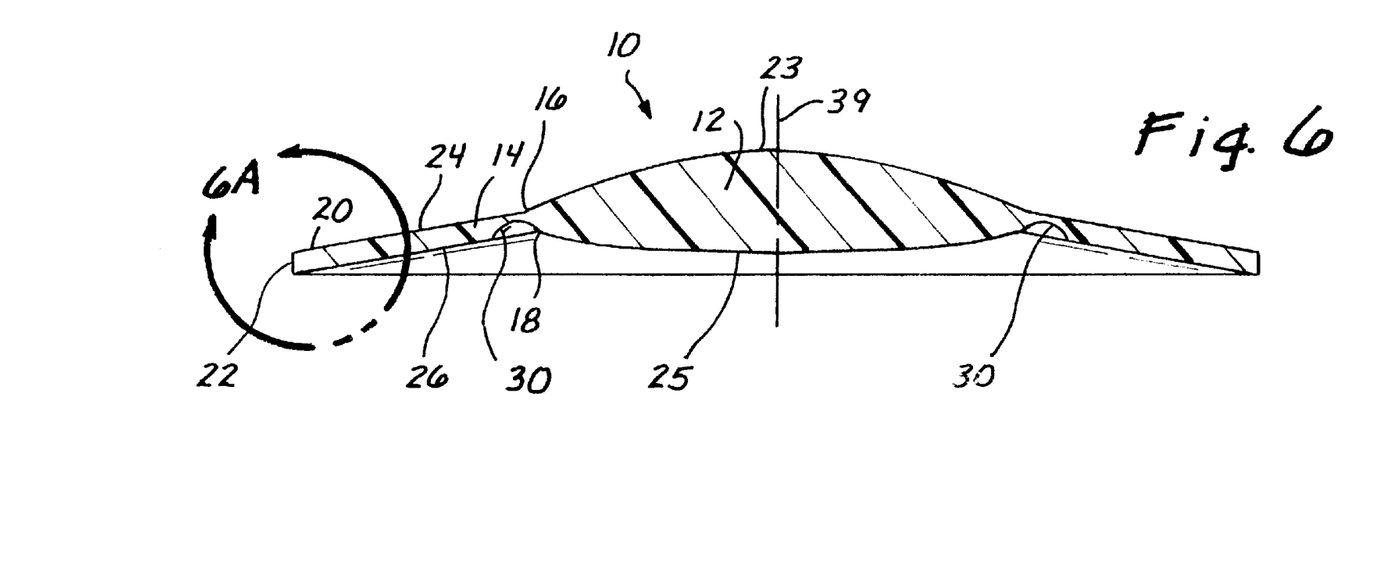
FIG. 6 is a cross-sectional view taken generally along line 6—6 of FIG. 4.

As best seen in FIG. 6, when IOL 10 is at rest, the optic 12 is positioned or vaulted anteriorly relative to the distal end region 20 of member 14. In other words, the anterior surface 23 of optic 12 is anterior of the anterior surface 24 of member 14 at distal end region 20 and/or the posterior surface 25 of the optic is anterior of the posterior surface 26 of the member at the distal end region.

The optic 12 may be constructed of rigid biocompatible materials, such as polymethyl methacrylate (PMMA), or flexible, deformable materials, such as silicone polymeric materials, acrylic polymeric materials, hydrogel polymeric materials and the like, which enable the optic 12 to be rolled or folded for insertion through a small incision into the eye. Although the optic 12 as shown is a refractive lens body, the present IOLs can include a diffractive lens body and such embodiment is included within the scope of the present invention.

Optic 12 is prescribed for the wearer of IOL 10 with a baseline or far (distance) diopter power for infinity.

Figure 5:
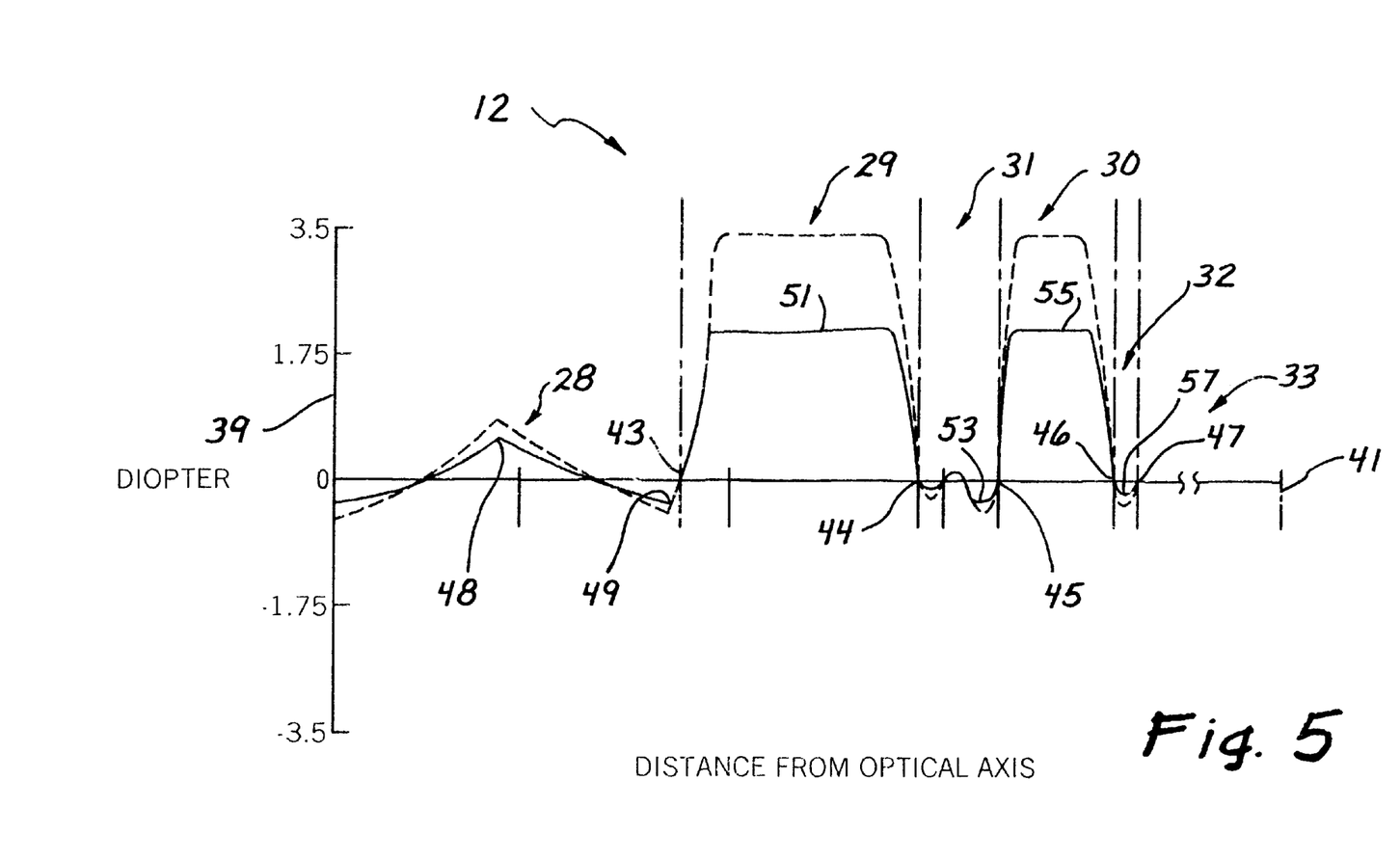
FIG. 5 is a plot of the power of the lens body of the intraocular lens shown in FIG. 1 versus distance from the optical axis of the intraocular lens.

One important aspect of IOL 10 relates to the reduced add powers of the lens body 12. This can be seen in FIG. 5. The power curve for the lens body 12 is shown as a solid line in FIG. 5. Specifically, the add power or magnitude of the optical power relative to the baseline or "X" axis (abscissa) of FIG. 5 is reduced relative to the add power of a similar lens body, shown in dashed lines in FIG. 5, of a similar IOL adapted for use in a fixed position in an eye in which the natural lens has been removed. Such similar lens is not adapted for accommodating movement in the eye. Thus, the optical add power of the lens body 12 remains relatively closer to the baseline power (defined as the "X" axis in FIG. 5) as compared to the optical add power of the above-noted similar lens body of the non-accommodating similar IOL adapted for use in an eye in which the natural lens has been removed. Although the amount of reduction in the add power (relative to the above-noted non-accommodating similar lens adapted for use in an eye in which the natural lens has been removed) may be as little as about 10% or about 20%, such reduction in the add power is often in the range of about 30% to about 50% or about 60% or more.

This reduced add power of lens body 12, particularly with regard to intermediate vision correction regions, is of substantial importance in the present invention since the IOL 10 is effective to cooperate with the eye to provide a significant, effective degree of accommodating movement. As seen in FIG. 5, the maximum add power of lens body 12 is no greater than about the add power for intermediate vision correction. Of course, the add powers of the lens bodies of the IOLs in accordance with the invention can be varied depending on the particular application involved, for example, the specific needs of the patient, the amount or degree of accommodating movement of he lens body to be obtained, the condition of the patient's eye and the like factors. In general, however, the present invention allows the patient to have a more complete range of vision from distance through near, and preferably provides the patient with a substantially complete or full range of vision from distance through near.

Thus, IOL 10 is very effective when inserted into an eye that is into the eye of a subject (e.g., human) in which that natural lens has been removed. The reduced add powers of IOL 10 are effective, in combination with the accommodating movement provided by IOL 10 to yield substantially full accommodation, for example, for near distance.

The lens body 12 provides enhanced vision, particularly for near objects. Such enhanced near vision is provided without the need for spectacles or other vision aids which can have at least a perceived detrimental effect on the appearance of the subject.

An additional advantage of the reduced add power of IOL 10 is a reduction in the effects of halos around lights, for example, when viewed from a distance, at night.

In the embodiment of FIGS. 1 to 6A, the lens body 12 has a convex anterior surface 25 and a convex posterior surface 27; however, these configurations are merely illustrative. Although the vision correction powers may be placed on either of the surfaces 25 or 27, in this embodiment, the anterior surface 25 is appropriately shaped to provide the desired vision correction powers.

With particular reference to FIG. 5, the lens body 12 has a central zone 28, inner and outer annular intermediate zones 29 and 30 and annular far zones 31, 32 and 33. In this embodiment, the central zone 28 is circular and the peripheries of the annular zones 29–33 are circular. The annular zones 29–33 circumscribe the central zone 28 and the zones are contiguous. The zones 29–33 are concentric and coaxial with the lens body 12.

The zones 28–33 are used in describing the vision correction power of the lens body 12, and they are arbitrarily defined.

FIG. 5 shows one manner in which the vision correction power of the lens body 12 varies from the center or optical axis 39 of the lens body to the circular outer periphery 41 of the lens body. In FIG. 5, the vertical or "Y" axis (ordinate) represents the variation in diopter power of the lens body 12 from the baseline or far vision correction power, and the "X" or horizontal axis shows the distance outwardly from the optical axis 39, for example, in millimeters. Thus, the zero-diopter or baseline power of FIG. 5 is the power required for far vision, at infinity, for the IOL 10. The power variation shown in FIG. 5 is applicable to any surface point on lens body 12 at a fixed radial distance from the optical axis 39. In other words, the power at any given radial distance from the optical axis 39 is the same.

The central zone 28 extends from the optical axis 39 to a circular periphery 43, the inner annular intermediate zone 29 is considered as extending from the periphery 43 to a circular periphery. 44, and the outer annular intermediate zone is considered as extending from a periphery 45 to a periphery 46. The annular far zone 31 extends between the peripheries 44 and 45, and the annular far zone 32 extends from the periphery 46 radially outwardly to a periphery 47. The annular zone 33 extends from the periphery 47 radially outwardly to the outer periphery 41 of the lens body 12.

The negative diopter powers at the optical axis and the point 49 are of less power than is required for far vision and may be considered as far, far vision correction powers. The actual correction provided by the plurality of optical powers will vary and depends, for example, on the amount of residual accommodative ability present in natural lens 50, among other factors.

The power curve of the central zone 28 reaches a high point at apex 48. The optical power curve configuration of central zone 28 provides a mean power in the central zone for far or distant vision.

Within the inner annular intermediate zone 29, the vision correction power varies from the periphery 43 to a plateau 51, and from the plateau, the vision correction power varies back to the periphery 44 at the baseline. In the far zone 31, the vision correction power increases very slightly above the baseline and then proceeds to a far, far negative vision correction power at a point 53 at which the vision correction power reverses and returns to the baseline at the periphery 45.

In the outer annular intermediate zone 30, the power varies from the periphery 45 to a plateau 55 and returns from the plateau 55 to the baseline at the periphery 46. In the far zone 32, the power dips slightly below the baseline to a point 57 in the far, far correction region and then returns to the baseline at the outer periphery 47. The dips below the baseline to the points 53 and 57 in the far zones 31 and 32 help support an increased depth of the focus of the central zone 28.

The far zone 33 has a vision power that lies along the baseline and is configured for far vision.

The IOL 10 can be inserted into the capsular bag of a mammalian eye using conventional equipment and techniques, for example, after the natural crystalline lens of the eye is removed, using a phaceomulsification technique. The IOL 10 preferably is rolled or folded prior to insertion into the eye, and is inserted through a small incision, on the order of about 3.2 mm or about 3.5 mm, into the eye and is located in the eye 40, as shown in FIGS. 1 to 3.

Figures 1, 2, 3:
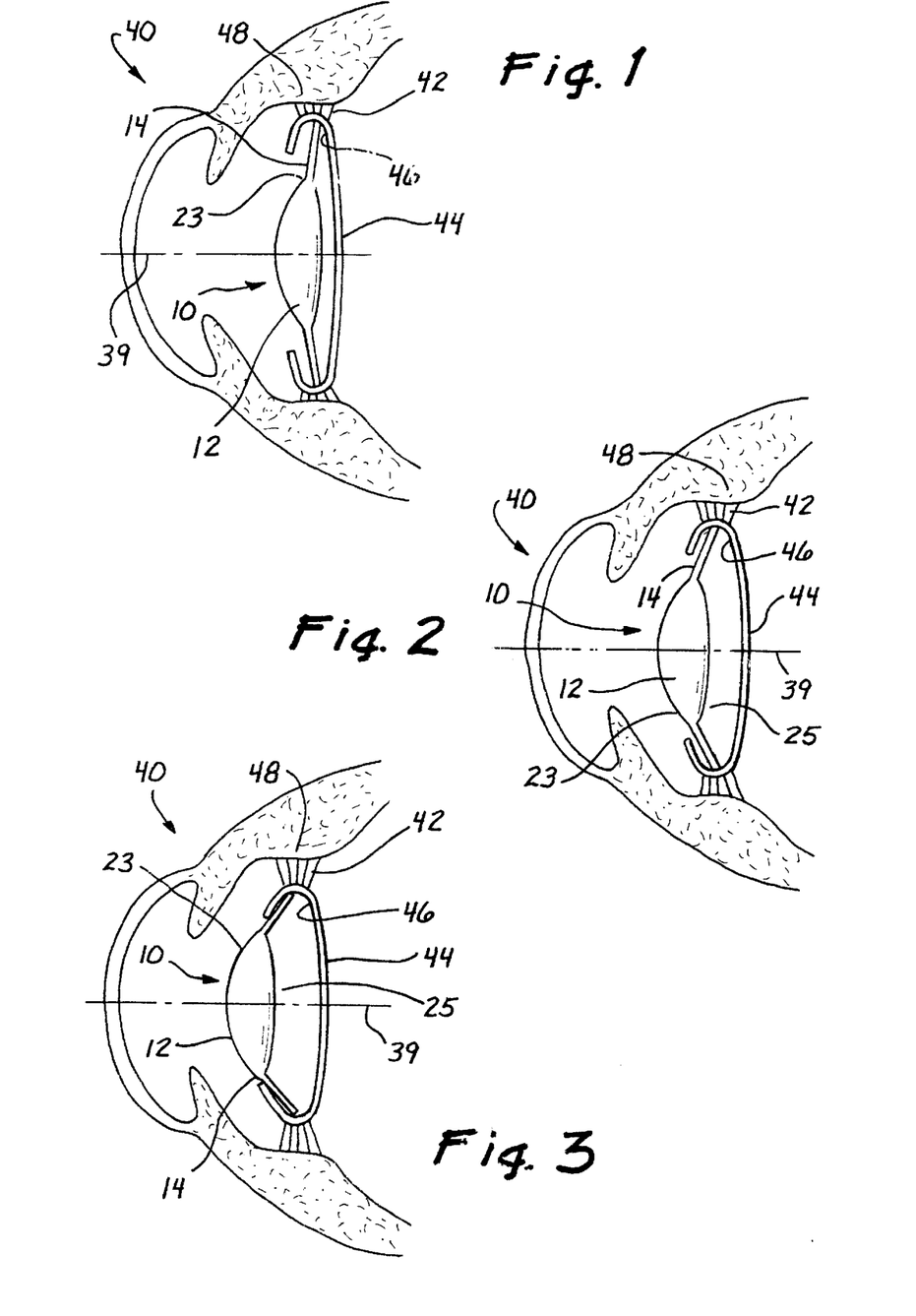
FIG. 1 is a fragmentary sectional view of an eye in which an IOL in accordance with the present invention has been implanted, with the lens being located in a posterior rest position in the eye.
FIG. 2 is a fragmentary sectional view of an eye in which the IOL shown in FIG. 1 has been implanted, with the lens being located in an intermediate position in the eye.
FIG. 3 is a fragmentary sectional view of an eye in which the IOL shown in FIG. 1 has been implanted, with the lens being located in an anterior position in the eye.
Figure 4:
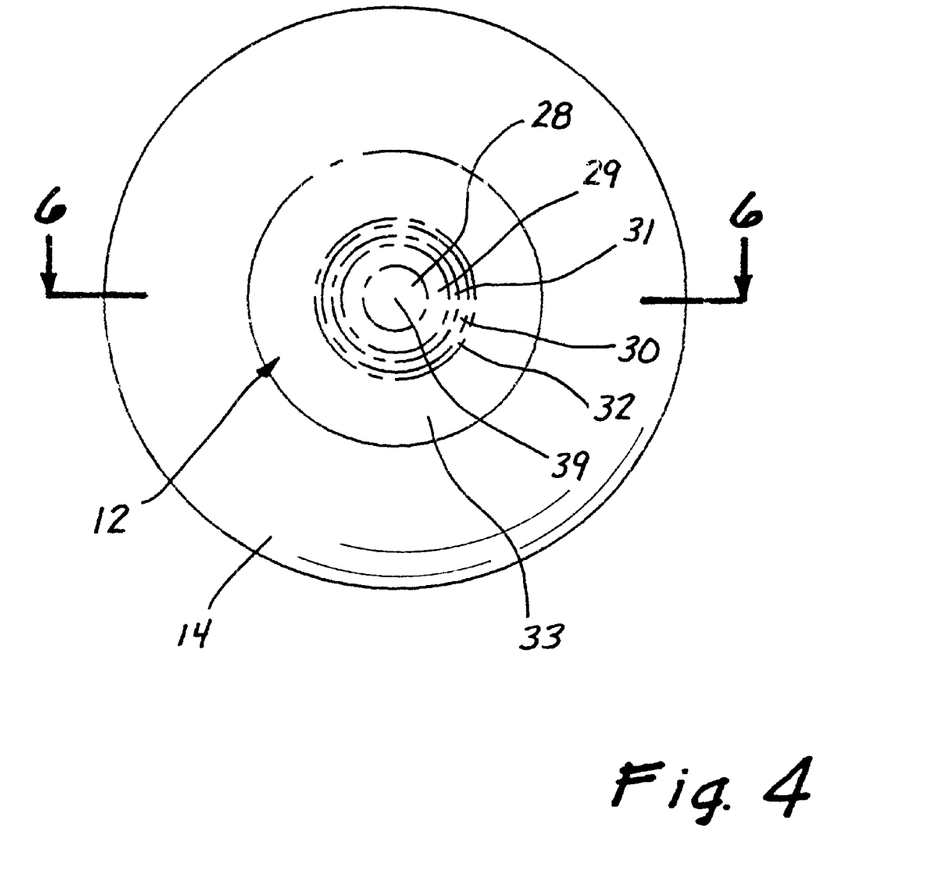
FIG. 4 is a front view of the IOL shown in FIG. 1.

The IOL 10 in the eye 40, as shown in FIG. 1, is located in a posterior position in the capsular bag 42 with zonules 42 under tension. The configuration of IOL 10, in particular with regard to the anterior vaulting of the optic 12, allows the IOL to be in the posterior-most position in the eye with the optic in close proximity to or even contacting the posterior capsule 44. However, in the posterior-most position the IOL 10 does not cause substantial stretching of the posterior capsule 44. The natural elasticity of the capsular bag preferably is substantially maintained and is effective in providing accommodating movement of the IOL 10.

The IOL 10 is positioned so that the optic 12, in cooperation with the eye 40, can be moved axially, substantially along optical axis 39 in the eye to provide accommodation.

The distal end region 20 of member 14 is in contact with the interior wall 46 of the capsular bag 44. Over time, the distal end region 20 of the member 14 may become affixed to the capsular bag 44, although this is not necessary to obtain benefits in accordance with the present invention. The member 14, in the eye 40, cooperates with the eye to effect accommodating movement of the optic 12, preferably upon radial, such as diametrical, compression of the IOL 10 by the elastic capsular bag 44 of the eye.

The IOL 10 should be sized to facilitate the movement of the optic 12 in response to the action of ciliary muscle 48 and zonules 42. For example, if the optic 12 is too large, the amount of accommodating movement will be unduly restricted. Of course, if the IOL 10 is too small, the optic 12 will be ineffective to focus light on the retina of the eye 40, may cause glare and/or the flexible member 14 may not cooperate with the eye to effect the desired amount of accommodating movement. If the IOL 10 is to be included in an adult human eye, the optic 12 preferably has a diameter in the range of about 3.5 mm to about 7 mm, more preferably in the range of about 5 mm to about 6 mm. and the IOL has an overall maximum diameter, with the member 14 in the unflexed or at rest state, in the range of about 8 mm to about 11 mm or about 12 mm.

The zonules 42 and the ciliary muscle 48 are effective to reduce or increase the equatorial diameter of the capsular bag 44 and thereby move the IOL 10 included in the bag anteriorly or posteriorly, respectively. Thus, relaxation of the ciliary muscle 48 causes the zonules 44 to increase the equatorial diameter of the capsular bag 44, resulting in IOL 10 moving posteriorly into a posterior position, as shown in FIG. 1.

With IOL 10 in the posterior position, as shown in FIG. 1, far away or distant objects are brought into focus.

If a near object is to be viewed, the ciliary muscle 48 contracts or constricts causing a reduction in the tension of the zonules 42, which allows the equatorial diameter of the capsular bag 44 to reduce. The IOL 10 is thereby diametrically compressed and moved anteriorly, as shown in FIG. 3.

The present IOL 10 because of the multifocal lens body 12 and movability in cooperation with the eye to provide for a substantially complete range of vision, that is from distance focus through near focus. The movement of IOL 10 advantageously occurs in response to action of the ciliary muscle 48, zonules 42 and capsular bag 44 which action is substantially similar to that which effects accommodation in an eye having a natural crystalline lens.

IOL 10 is such that the amount of positive or near accommodating movement preferably is at least about 1.0 diopter, more preferably, about 1.5 diopters to about 2 diopters or more. Looked at from another perspective, the configuration and sizing of IOL 10 preferably is effective to provide an amount of axial movement anteriorly in the eye of at least about 0.5 mm or at least about 0.75 mm, more preferably about 0.75 mm to about 1.0 mm, or more, for example, with about 1 mm of reduction in the equatorial diameter of the capsular bag 44 caused by the action of the ciliary muscle 48 and zonules 42. This amount of axial movement is based on an initial position of the IOL 10 in the posterior position, as shown in FIG. 1.

Figure 6A:
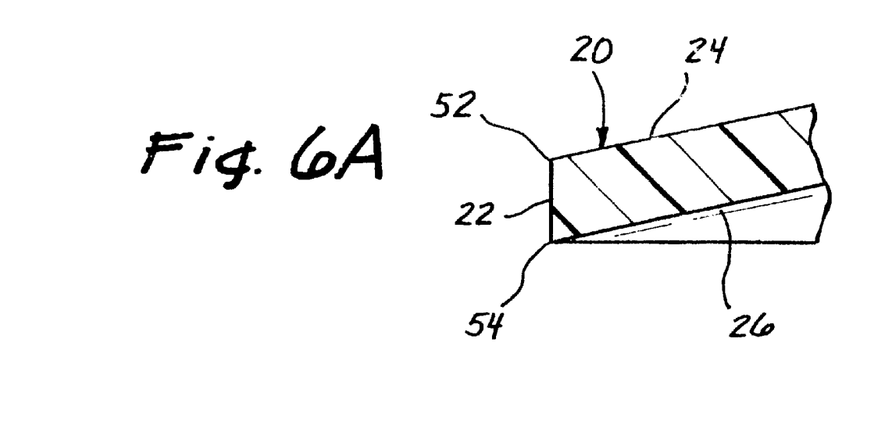
FIG. 6A is a cross-sectional view taken generally along arc 6–6A of FIG. 6.

As best shown in FIG. 6A, the intersections of peripheral edge 22 with the anterior face 24 and posterior face 26 of member 14 also are at substantially 90° relative to the optical axis of the IOL 10. These sharp corners 52 and 54, which involve substantial discontinuities, rather than continuous or curved transitions, between the peripheral edge 22 and anterior face 24 and posterior face 26, respectively, have been found to be effective in inhibiting or retarding cell migration or growth from the eye onto or over the optic 12 of the IOL 10.

FIGS. 7 to 9C illustrate an ophthalmic lens system in accordance with the present invention. Except as expressly described herein, the IOLs included in this system, designated first IOL 110 and second IOL 210, are structured and function, for example, during implantation in the eye, similarly to IOL 10. Components of first IOL 110 and second IOL 210 which correspond to components of IOL 10 are indicated by the same reference numeral increased by 100 and 200, respectively.

One primary difference between IOL 10 and first IOL 110 and second IOL 210 relates to the power curves of the first and second lens bodies or optics 112 and 212, respectively.

Figure 7:
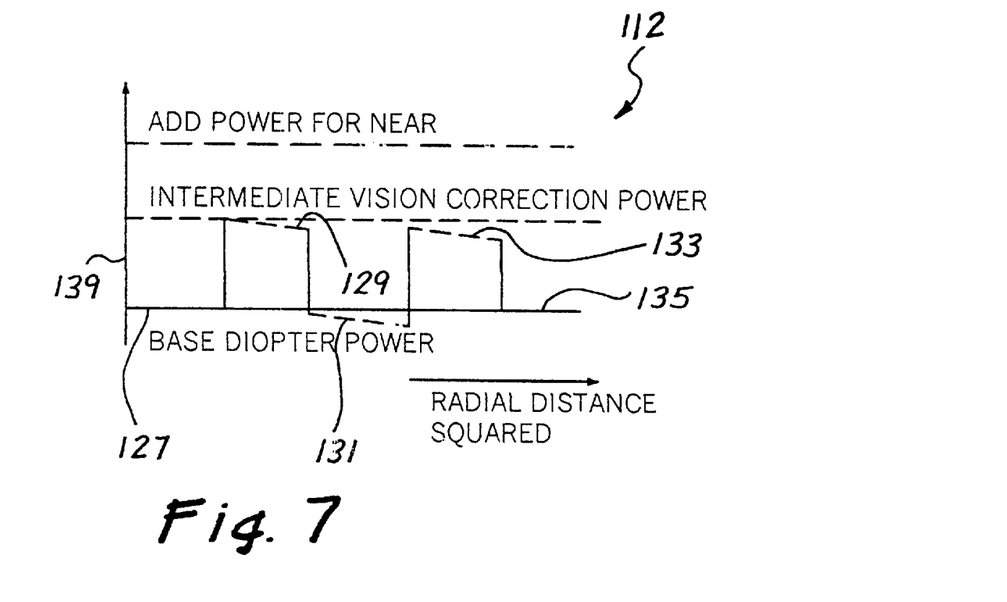
FIG. 7 is a plot of add power of an IOL having a distance biased optic in accordance with the present invention versus radial distance squared from the optic axis of the IOL.
Figure 8:
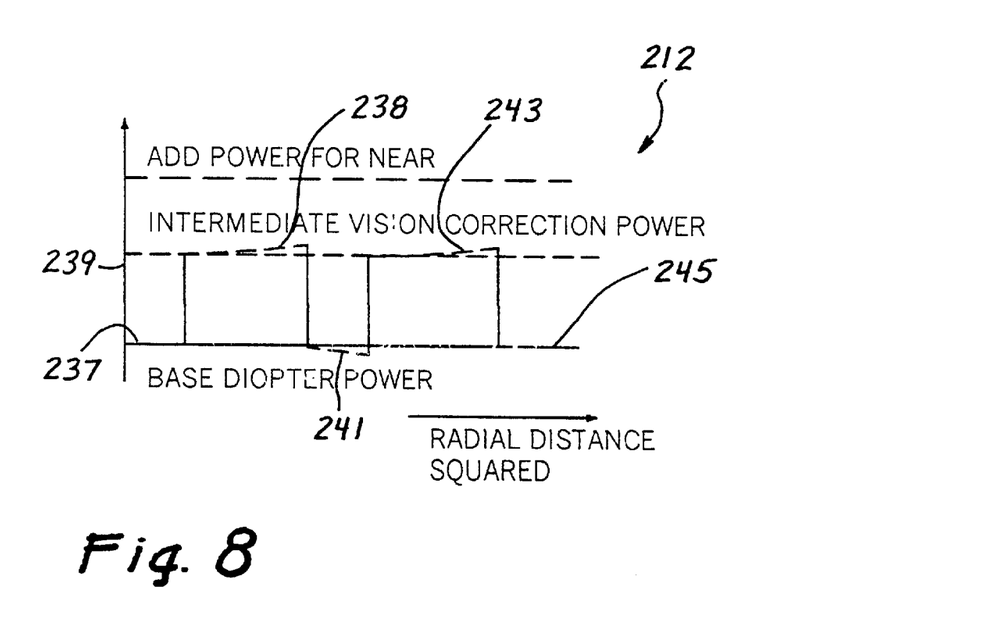
FIG. 8 is a plot similar to FIG. 7 for an intermediate biased IOL to be used with the distance biased IOL of FIG. 7.

FIG. 7 shows the power curve of first optic 112 of first IOL 110 and FIG. 8 shows the power curve of second optic 212 of second IOL 210. First IOL 110 and second IOL 210 together form a lens pair or ophthalmic lens system for improving the vision of a patient whose natural lenses have been removed, that is a pseudophakic patient.

The optical characteristics of the first and second lens bodies 112 and 212 are different as described more specifically herein below. However, except for the optical characteristics of the lens bodies 112 and 212, the IOLs 110 and 210 may be identical, for example, as described above with regard to IOL 10.

With respect to optical characteristics, it can be seen from FIG. 7 that the first optic 112 has a central zone 127 and additional optical zones 129, 131, 133 and 135. In this embodiment, the central zone 127 is circular and the lens body 112 has a circular outer periphery. Also, in this embodiment, the additional optical zones 129, 131, 133 and 135 are annular and concentric with the central zone 127, and all of these zones are centered on the optical axis 139.

With reference to FIG. 7, it can be seen that the central zone 127 and the outermost annular zone 135 have a baseline or base diopter power which is the power required by the patient for distance vision correction and is considered as a zero add power. It should also be noted that the diopter power variation shown in FIGS. 7 and 8 (as well as FIG. 5) is applicable to any point on the surface of the lens bodies at a fixed radial distance from the associated optical axes. In other words, the power at any given radial distance from the optical axis 139 is the same, and the power at any given radial distance from the optical axis 239 is the same.

The annular zone 131 has about the power required for distance vision correction. Although the annular zone 131 could have precisely the power required for distance vision correction, i.e. zero add power, in this embodiment, the power of the annular zone 131 decreases progressively and slightly from the outer edge of the zone 129 to about the inner edge of the zone 133 to provide spherical aberration correction. Thus, although the optical power of the zone 131 does diminish in a radial outward direction in this fashion, it nevertheless is considered to be about the power needed for far or distance vision correction for the pseudophakic patient. For example, the vision correction power of the zone 131 may decrease from a zero add power to about 0.25 diopter below the base diopter power.

The zones 129 and 133 have greater vision correction power than the zones 127, 131 and 135 and are preferably at or about the power required for intermediate vision correction. In terms of a single power, the power for intermediate vision correction would be halfway between the base diopter power and the add power for near vision correction. By way of example, if the base diopter power is considered to be zero add and the add power for near vision correction is considered to be 3 diopters, then the power for intermediate vision correction would be 1.5 diopters of add power. More broadly, however, the intermediate vision correction power may be taken to embrace a zone of from about 0.5 diopter to about 1.75 diopters .and preferably that zone may be from about 1diopter to about 1.5 diopters. When thus considered, the power of the zones 129 and 133 would all be add powers for intermediate vision correction.

The vision correction power in the zone 129 reduces progressively and slightly in a radial outward direction from an add power for intermediate vision correction such as 1.5 diopters as shown in FIG. 7 to a slightly less add power for intermediate vision correction so as to provide for spherical aberration correction. Again, to correct for spherical aberration, the maximum power of the zone 133 is about the minimum power of the zone 129 and reduces progressively and slightly in a radial outward direction as shown in FIG. 7. By way of example, the power of the zone 129 may decrease linearly from about 1.5 diopters to about 1.25 diopters and the vision correction power of the zone 133 may reduce linearly in a radial outward direction from about 1.25 diopters to about 1.0 diopter. Thus, all of the powers of the zones 129 and 133 may be considered as add powers for intermediate vision correction. Thus, it can be readily seen from FIG. 7 that the maximum power of any region of the first optic 112 is no greater than about the power for intermediate vision correction.

The annular areas of the distance correction zones 127, 131 and 135 are intended to be larger than the annular areas of the intermediate power zones 129 and 133. Moreover, there are three of the distance power zones 127 and 135 and only two of the intermediate vision correction zones 129 and 133, although other numbers of these zones may be employed, if desired. Thus, a larger surface of the first optic 112 is dedicated to focusing or directing light to a far focus region than any other focus region. Accordingly, the first IOL 110 provides very good visual acuity from distance to intermediate, and provides better visual acuity for objects at infinity than the second IOL 210. The first IOL 110 is optimized for distance to intermediate vision.

With reference to FIG. 8, the second optic 212 of the second IOL 210 has a circular outer periphery, an optical axis 239, a circular central zone 237 and optical zones 238, 241, 243 and 245 which are preferably annular and concentric with the central zone 237. All of these zones 237, 238, 241, 243 and 245 are centered on the optical axis 239. The nature of the optical zones 237, 238, 241, 243 and 245 makes the second optic 212 optically different from the first optic 112, but except for this the first and second IOLs 110 and 210 may be identical, if desired. It can be seen from FIG. 8 that the central zone 237 and the outer annular zone 245 have the base diopter power, i.e., the power required for distance vision correction for the patient or a zero add power. The intermediate annular zone 241 has about the base diopter power. More specifically, the annular zone 241 has a maximum power which is the base diopter power and the vision correction power of this zone decreases progressively in a radial outward direction to a diopter power which is slightly less than the base diopter power in order to correct for spherical aberrations. By way of example, the minimum power of the zone 241 may be 0.25 diopter below the base diopter power.

The zones 238 and 243 have a vision correction power which is about the add power for intermediate vision correction. In each of the zones 238 and 243, the vision correction power increases progressively in a radial outward direction. For example, the minimum power of each of the zones 238 and 243 may be about 1.5 diopters and the maximum power at the radial outer edge of each of these zones may be about 1.75 diopters.

In this embodiment, the second IOL 210 has enhanced intermediate to near vision. In this regard, the intermediate power zones 238 and 243 are provided with optical aberrations which increase the depth of focus of such zone. Specifically, the progressively increasing vision correction powers in a radial outward direction in these zones 238 and 243 increase the spherical aberrations which, in turn, increase the depth of focus by effectively creating stronger diopter power at radial outward locations in each of these zones to therefore allow closer objects to be in focus. This has the effect of increasing the near visual quality at the expense of the intermediate image quality, thereby raising the overall image quality as described more fully hereinbelow in connection with FIGS. 9A–C. Thus, this increased depth of focus contributes to making the second IOL 210 biased or enhanced for intermediate to near vision and certainly more enhanced for intermediate to near vision than the first IOL 110 which has spherical aberration correction. Stated differently, the second IOL 210 provides better visual acuity from intermediate to near than the first IOL 110. Conversely, the first IOL 110 is biased or optimized for distance to intermediate vision and certainly provides better visual acuity for distance to intermediate than the second IOL 210.

In addition a larger portion of the area of the second optic lens 212 is used to direct light to an intermediate focus region so as to contribute to the second optic lens body 212 having better visual acuity from intermediate to near than the first IOL 110. Thus, the combined areas, that is the combined annular areas, of the zones 238 the zones 237, 241 and 245, and this is shown in FIG. 8. Consequently, more of the incident light is directed to an intermediate focus region than to a distance or far focus region, and this also contributes to the second IOL 210 intermediate to near than the first IOL 110 and to providing enhanced intermediate-to-near image quality. As compared with the first IOL 110, it can also be seen from FIGS. 7 and 8 that the area of each of the zones 238 and 243 of the second IOL 210 is larger than the area of either of the zones 129 and 133 of the first IOL 110. This also contributes to the second IOL 210 having better visual acuity from intermediate to near than the first IOL 110. Second IOL 210 is intermediate biased, whereas first IOL 110 is distance biased.

From FIGS. 7 and 8, it is apparent that the maximum powers of any region of either of the first and second IOLs 110 and 210 are less than the add power required for full near vision correction, the latter being an add power which is at least greater than about 1.75 diopters of add power, and is typically between about 2.0 diopters or about 2.5 diopters to about 3.0 diopters or more of add power. Also, the maximum powers of any region of either of the first and second IOLs 110 and 210 are no greater than about the intermediate vision correction power. The plots of FIGS. 7 and 8 represent power curves showing how the vision correction power of each of the first and second IOLs 110 and 210 changes in a radially outward direction from the optical axes 139 and 239, respectively, and it is apparent that the power curves of FIGS. 7 and 8 are different. Moreover, the differences in these power curves contribute to the range of vision characteristics of first and second IOLs 110 and 210.

The first and second multifocal IOLs 110 and 210 are implanted in the eyes of a patient after the natural lenses have been removed. The first IOL 110 is distance biased and provides better visual acuity for objects at infinity than the second IOL 210. The second IOL 210 is intermediate biased and provides better visual acuity from intermediate to near distances than the first IOL 110. The maximum power of the second IOL 210 is less than the add power required for near vision correction for the patient. With specific reference to the embodiments shown in FIGS. 7 and 8, the method includes implanting the first and second IOLs 110 and 210 in the eyes, respectively, of the patient. This implantation follows the removal of the natural lenses from the eyes. The patient is thus provided substantially full range accommodation by the combination of the multifocal optics 112 and 212 and the accommodating movement of the first and second IOLs 110 and 210, respectively in each of the patient's eyes.

Figure 9A:
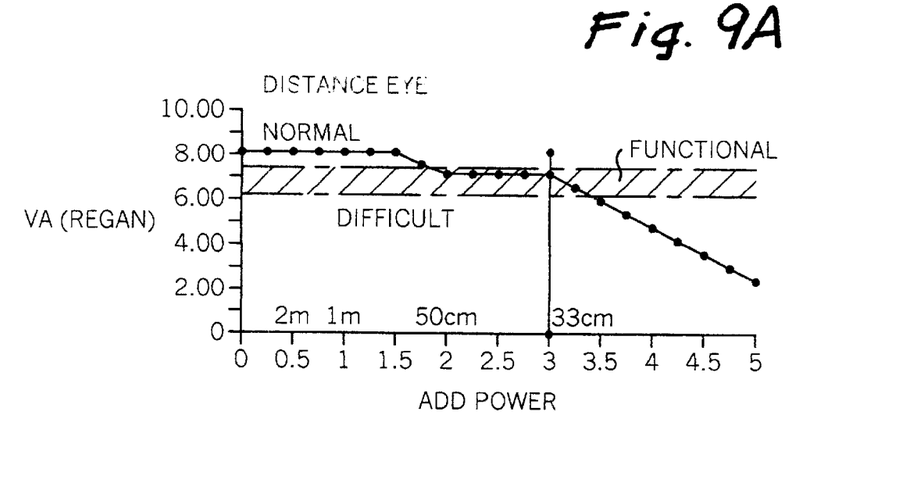
FIG. 9A is a plot of visual acuity versus add power for the distance based IOL of FIG. 7 when implanted in a pseudophakic eye.
Figure 9B:
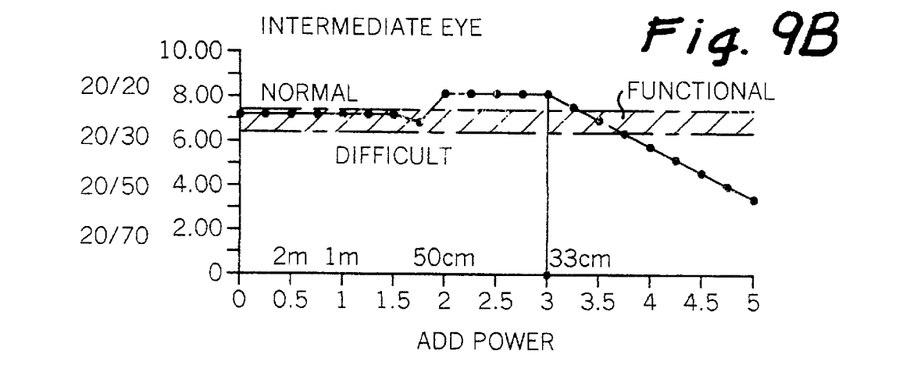
FIG. 9B is a plot similar to FIG. 9A for the intermediate biased IOL of FIG. 8 implanted in a pseudophakic eye.
Figure 9C:
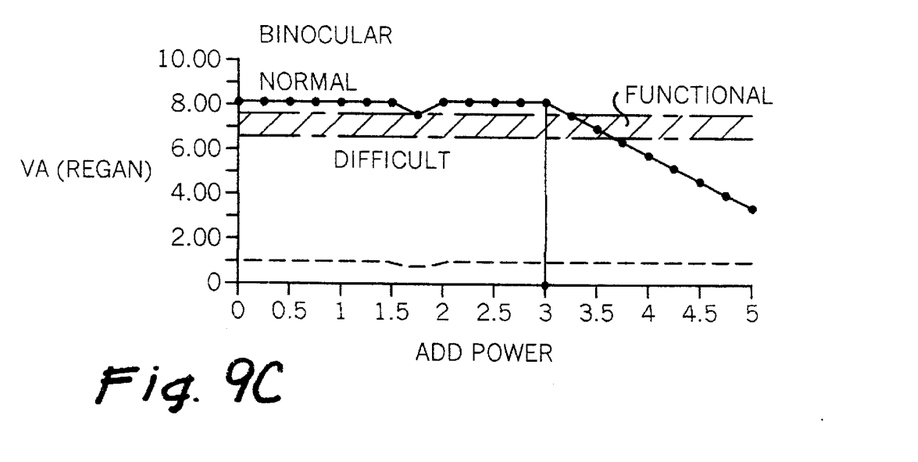
FIG. 9C is a plot similar to FIG. 9A for binocular combination of the distance biased IOL of FIG. 7 and the intermediate biased IOL of FIG. 8 when implanted in pseudophakic eyes, respectively.

FIGS. 9A–C are of use in gaining a further understanding of how the first and second IOLs 110 and 210 work in cooperation with the eye to provide the patient with an enhanced range of vision. These figures are through-focus-acuity charts for a pseudophakic patient who requires 3 diopters of total accommodation and who has the first and second IOLs 110 and 210 implanted in the posterior capsules, respectively, of his/her eyes. These figures also consider that the accommodating movement of the first and second IOLs 110 and 210 effectively provide 1.5 diopters of accommodation.

Each of these figures shows visual acuity (VA) along the ordinate and add power in diopters along the abscissa. In addition, the reciprocal of the diopter add power in meters is also shown along the abscissa. The add power is the add power required by a patient with no accommodation at the corresponding distance indicated on the abscissa. The units for visual acuity or VA are Regan, and in FIG. 9B an approximate correspondence to the 20/x scale is shown. A visual acuity of about 8 corresponds to 20/20 and is considered normal vision. Functional vision is considered to be about 20/30 up to nearly 20/20, and is shown by the cross hatched band in FIGS. 9A–C. Although functional vision is clinically not normal, it may seem normal to the patient. Below about 20/30 vision becomes progressively more difficult and somewhat about 3 Regan or slightly worse than 20/60 there is essentially no usable visual acuity. The visual acuity plots of FIGS. 9A–C are theoretical.

FIG. 9A shows the visual acuity with the distance eye, i.e., the eye in which the optimized distance to intermediate first IOL 110 is implanted. In a similar fashion, FIG. 9B shows the visual acuity in the intermediate eye, i.e., the eye in which the enhanced intermediate to near second IOL 210 is implanted, and FIG. 9C shows the binocular visual acuity, i.e., the visual acuity for both eyes with the first and second IOLs 110 and 210 implanted. As shown in FIG. 9C, the binocular visual acuity remains normal for the full range from distance to a very close reading distance of 33 centimeters, i.e., zero to 3 diopters of add power.

Because of the reduced add power in both of the first and second IOLs 110 and 210, halos in either eye should be significantly reduced. Also, the between-eye visual acuity difference never exceeds half an acuity line which is approximately 20% of the between-eye visual acuity difference experienced in monovision with a 2.5 diopter add. Thus, the potential for symptoms associated with failure of monovision is significantly reduced.

While this invention has been described with respect of various specific examples and embodiments, it is to be understood that the invention is not limited thereto and that it can be variously practiced within the scope of the following claims.

What is claimed is:

1. An intraocular lens for implantation in an eye of a patient comprising:
   a multifocal optic having a maximum add power which is less than the add power required for full near vision for a pseudophakic eye; and
   a movement assembly coupled to the optic and adapted to cooperate with the eye of the patient to effect accommodating movement of the optic in the eye, the movement assembly being positioned relative to the optic so that, with the intraocular lens at rest, the optic vaults anteriorly of the distal end region of the movement assembly.

2. An intraocular lens as defined in claim 1 wherein the maximum add power is about the add power required for intermediate vision for a pseudophakic eye.

3. An intraocular lens as defined in claim 1 wherein the optic has add powers for providing distance and intermediate vision for a pseudophakic eye and the movement assembly is adapted to provide sufficient movement of the optic to obtain near vision for a pseudophakic eye whereby the patient has a range of vision of distance through near.

4. An intraocular lens as defined in claim 1 wherein the maximum add power is no more than about 1.5 diopters and the movement assembly is adapted to provide at least about 1.0 diopters of accommodation.

5. An intraocular lens as defined in claim 1 wherein the movement assembly is adapted to provide at least about 0.50 millimeter of said accommodating movement.

6. An intraocular lens as defined in claim 1 wherein the optic has a distance vision correction power for infinity.

7. An intraocular lens as defined in claim 1 wherein the movement assembly circumscribes the optic and comprises a member including a proximal end region coupled to the optic and a distal end region extending away from the optic and adapted to contact a capsular bag of the eye.

8. An intraocular lens as defined in claim 1 which is deformable for insertion through a small incision in the eye.

9. An intraocular lens as defined in claim 1 wherein the movement assembly includes a hinge assembly positioned proximally of the distal end region.

10. A method comprising:
    providing the intraocular lens of claim 1; and
    placing the intraocular lens in the eye of a patient so that the eye can cooperate with the intraocular lens to move the optic to provide accommodation.

11. An ophthalmic lens system for implantation in the eyes of a patient comprising:
    first and second multifocal optics, each of said optics having an add power, the maximum add power of the first optic being less than the add power required for full near vision for a pseudophakic eye, and the first optic provides better visual acuity for objects at infinity than the second optic; and
    first and second movement assemblies coupled to the first and second optics, respectively, and adapted to cooperate with the eyes, respectively, of the patient to effect accommodating movement of the first and second optics.

12. An ophthalmic lens system as defined in claim 11 wherein each of said optics has an optical axis, the power of each of said first and second optics changes along a power curve and the power curve for the first optic is different from the power curve for the second optic.

13. An ophthalmic lens system as defined in claim 11 wherein each of said optics has an optical axis, the power of each of said first and second optics changes along a power curve and the power curve for the first optic is substantially the same as the power curve for the second optic.

14. An ophthalmic lens system as defined in claim 11 wherein the second optic has a maximum add power and the maximum add powers of the first and second optics are no greater than about an intermediate add power for intermediate vision for a pseudophakic eye.

15. An ophthalmic lens system as defined in claim 11 wherein each of the first and second optics has a distance vision correction power for infinity.

16. An intraocular lens as defined in claim 11 wherein each of the first and second movement assemblies circumscribes the associated optic and comprises a member including a proximal end region coupled to the optic and a distal end region extending away from the optic and adapted to contact a capsular bag of an eye.

17. A method comprising:
    providing an ophthalmic lens system of claim 11;
    placing the first optic and the first movement assembly of the ophthalmic lens system in the first eye of a patient so that the eye can cooperate with the first movement assembly to move the first optic to provide accommodation; and
    placing the second optic and the second movement assembly of the ophthalmic lens system in the second eye of a patient so that the eye can cooperate with the second movement assembly to move the second optic to provide accommodation.

18. An ophthalmic lens system for implantation in the eyes of a patient comprising:
    first and second multifocal optics, each of said optics having an add power, the maximum add power of the first optic being less than the add power required for full near vision for a pseudophakic eye, the first optic being biased for distance vision and the second optic being biased for intermediate vision; and first and second movement assemblies coupled to the first and second optics, respectively, and adapted to cooperate with the eyes, respectively, of the patient to effect accommodating movement of the first and second optics.

19. An ophthalmic lens system for implantation in the eyes of a patient comprising:

first and second multifocal optics, each of said optics having an add power, the maximum add power of the first optic being less than the add power required for full near vision for a pseudophakic eye, the add power of the second optic is an intermediate add power for intermediate vision for a pseudophakic eye and the best visual acuity provided by the second optic is for objects at intermediate distances; and first and second movement assemblies coupled to the first and second optics, respectively, and adapted to cooperate with the eyes, respectively, of the patient to effect accommodating movement of the first and second optics.

* * * * *